United States Patent
Nelson

(10) Patent No.: US 6,531,461 B1
(45) Date of Patent: Mar. 11, 2003

(54) MEDICAMENT FOR THE TREATMENT OF DIABETES

(76) Inventor: Louis Obyo Obyo Nelson, Plot 574 Yakubu Gowan Crescent, Asokoro Abuja (NG)

( * ) Notice: Subject to any disclaimer, the term of this patent is extended or adjusted under 35 U.S.C. 154(b) by 0 days.

(21) Appl. No.: 09/873,560

(22) Filed: Jun. 4, 2001

(51) Int. Cl.⁷ .................. A61K 31/58; A61K 31/585; A61K 31/56
(52) U.S. Cl. .................. 514/172; 514/172; 514/174; 514/175; 514/178
(58) Field of Search .................. 514/172, 174, 514/175, 178

(56) References Cited

U.S. PATENT DOCUMENTS 4,387,101 A  6/1983  Kawamatsu et al. ........ 424/270

FOREIGN PATENT DOCUMENTS

| WO | 9507694 | * 3/1995 |
| WO | WO 98/57636 | 12/1998 |

OTHER PUBLICATIONS

Schmittamann et al. (DN 121:153368, HCAPLUS, abstract of J. Prakt. Chem./Chem.–Ztg. (1994), 336,(3), 225–32).*
Ohigashi, Masanori et al. (DN 121:270, abstract of J. Chem. Ecol. (1994), 20(3), 541–53).*

* cited by examiner

Primary Examiner—Sabiha Qazi
(74) Attorney, Agent, or Firm—Barlow, Josephs & Holmes, Ltd.

(57) ABSTRACT

A series of compounds of general structure I and metal salts thereof. These compounds are useful in the treatment of diabetes mellitus and associated conditions when administered in an effective non-toxic dose in the form of a pharmaceutically acceptable composition resulting in cell regeneration.

General Structure 'A'

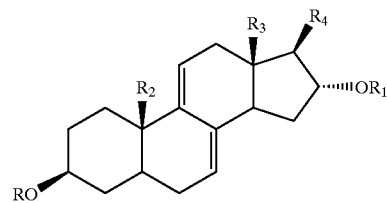

wherein for example,
R=H, $R_1$=H, $R_2$=Me, $R_3$=Me
and $R_4$=

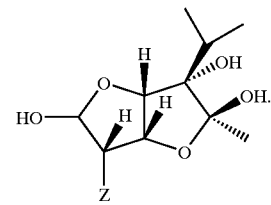

10 Claims, No Drawings

MEDICAMENT FOR THE TREATMENT OF DIABETES

TECHNICAL FIELD

The present invention relates to compounds for use as medicaments in the treatment of diabetes.

PRIOR ART

Diabetes is a potentially life threatening condition in mammals brought about by an inability of the mammals to produce insulin. Insulin, a polypeptide hormone produced in the pancreas of the mammal, controls the amounts of glucose present in the blood by stimulating the uptake of glucose by the muscle and adipose tissue.

The production of insulin is ultimately controlled by the brain. Biosynthesised insulin has been the drug of choice for the treatment of diabetes mellitus or hyperglycemia (the term imparted to an excess of glucose in the blood), for many years. Biosynthesised insulin is manufactured by recombinant DNA technology at a high cost.

The administration of biosynthesised insulin to the patient occurs via injection directly into the muscle, since it is partially digested if administered orally. This administration method further elevates costs due to the requirement for needles and furthermore, increases the likelihood of infection and/or contamination.

More recently thiazolidine derivatives, as described in U.S. Pat. No. 4,387,101, have been introduced for the treatment of hyperglycemia. However, there are some concerns relating to the toxicity of these derivatives.

WO9857636 teaches of an oral antidiabetic agent, rosiglitazone maleate which when administered in conjunction with insulin acts primarily by increasing insulin sensitivity.

None of the aforementioned methods of treatment offer any remission for diabetes. The present invention has been made from a consideration of this problem.

According to the present invention there is provided a compound for use as a medicament, having general structure 'A', and metal salts thereof;

General Structure 'A'

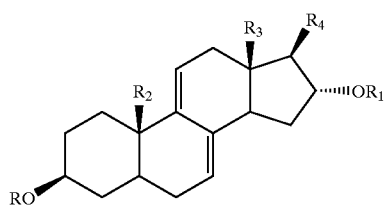

wherein R, $R_1$, $R_2$, $R_3$ and $R_4$ are any of the following combinations.

TABLE 1

N.B Z denotes the point at which substituent $R_4$ couples to general structure 'A'.

| R | $R_1$ | $R_2$ | $R_3$ | $R_4$ |
|---|---|---|---|---|
| H or 3-o-β-D-Glucopyranoside | H or alkyl $(C_1-C_4)$ or —OCOCH$_3$ | H or alkyl $(C_1-C_4)$ | H or alkyl $(C_1-C_4)$ | Substituent I, Substituent II, Substituent III, Substituent IV or Substituent V. | and wherein substituents I, II, III, IV and V and are as shown below:

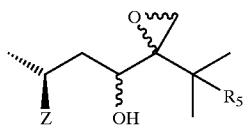

Substituent I

Where $R_5$ = OH or alkyl $(C_1-C_4)$

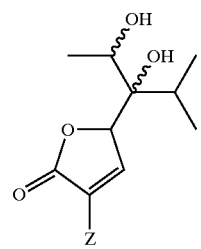

Substituent II

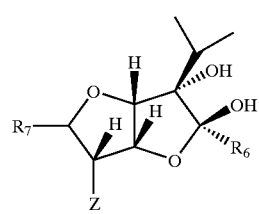

Substituent III

Where $R_6$ is H, OH, or Me
$R_7$ is H, OH or (O=)

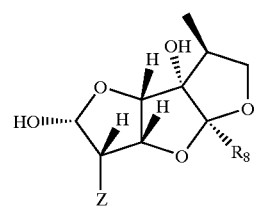

Substituent IV

Where $R_8$ is H or alkyl $(C_1-C_4)$

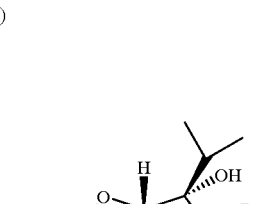

Substituent V

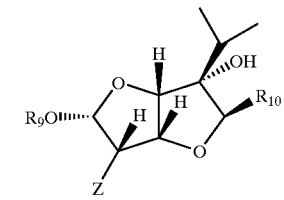

Where $R_9$ is H, Et, Me and $R_{10}$ is H, Et, and Me

DISCLOSURE OF INVENTION

It has been found that the compounds of the present invention, as isolated from the leaf of the common *Vernonia amygdalina* plant and having the general structure 'A', as identified in G. Igile et al., J. Nat. Prod., 1995, 58, 1438, R. Sanogo et al., Phytochemistry, 1998, 47, 73, M. Jisalca et al., Phytochemistry, 1993, 34, 409 and D. Ponglux et al., Chem. Pharm. Bull., 1992, 40, 553 are particularly useful for the treatment of hyperglycemia.

In general structure 'A', a number of sites are capable of substitution and modification. For example $R_1$ may be H or alkyl and $R_4$ may be a heterocyclic enone or a fused difuran system, as detailed hereinafter.

It has been found that the compounds of the present invention having general structure 'A' where R=H, $R_1$=H, $R_2$=Me, $R_3$=Me and $R_4$=substituent III in which $R_7$=OH and $R_6$=Me, or substituent I in which $R_5$=OH, or substituent IV in which $R_8$=Me or substituent II or substituent V in which $R_9$H and $R_{10}$=Me exemplified in table 1, are highly effective in the treatment of hyperglycemia.

Furthermore, the compounds of the present invention may bring about cell regeneration as trials involving hyperglycemic mammals have resulted in the restoration of complete insulin activity within six months.

It is thought that these compounds enhance insulin sensitisation and may even replace insulin whist initiating beta cell regeneration.

Advantageously, the compounds of the present invention exhibit no known toxicity when administered to either hyperglycemic or non-hyperglycemic mammals.

The compounds of the present invention may be used in the management of type I and type II diabetes mellitus.

The compounds of the present invention may be in the form of one or more cationic salts, for example sodium, potassium, lithium. The compounds may also be in the form of a hydrate or solvate.

The compounds of the present invention may be conveniently isolated and purified using conventional separation—purification, such as solvent extraction, phasic transfer or redistribution, concentration, concentration under reduced pressure, crystallisation, chromatography and recrystallisation.

Furthermore, since the compounds of the present invention are derived from the common *Vernonia amygdalina* plant, they are easily and cost effectively obtained, particularly when compared with the compounds of the prior art.

The compounds of the present invention may be administered by any convenient parenteral route.

Preferably, the compounds of the present invention will be administered orally. The dose may be varied depending upon the patient, but will generally be 100 mg, three times daily.

According to a second aspect of the present invention there is provided a pharmaceutical composition which may find utility in the treatment of hyperglycemia in mammals comprising a therapeutic amount of any of the compounds of the present invention and a pharmaceutically acceptable carrier excipient or diluent for example a sodium salt, glucose syrup, sugar solution, alcohol solution, CMC or starch.

According to a third aspect of the present invention there is provided a method for the treatment of hyperglycemia in mammals which utilises any of the compounds of the present invention.

The invention is illustrated with reference to the following preferred examples.

EXAMPLE 1

21,23:22,28-Diepoxystigmasta-7,92 (11)-diene-3,16, 21,24,28-pentol

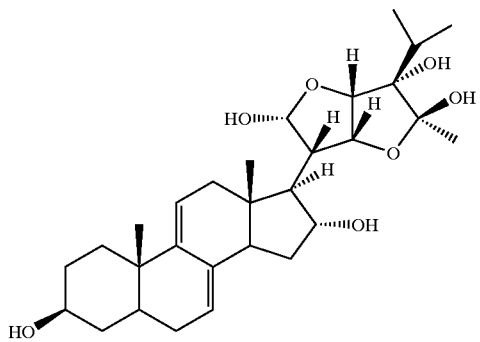

EXAMPLE 2

24,28-Epoxystigmasta-8,92 (11)-diene-3,16,23,25-tetrol

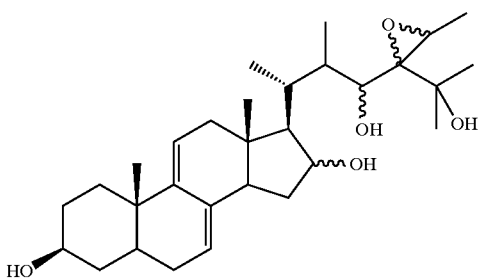

EXAMPLE 3

21,23:22,28;26,28-Triepoxystigmasta-7,92 (11)-diene-3,16, 21,24-tetrol

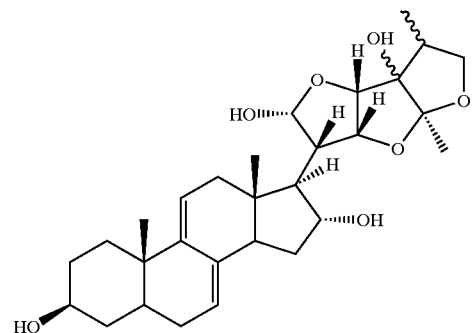

EXAMPLE 4

3,16,24,28-Tetrahdroxystigmasta-7,92 (11)-diene-21,23-olide

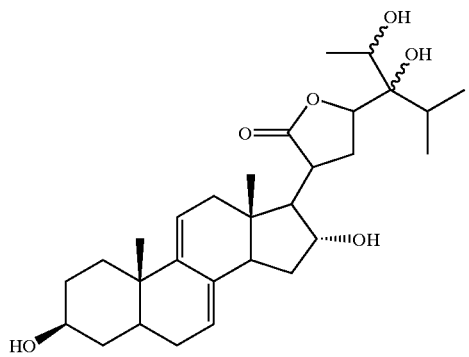

EXAMPLE 5

21,23:22, 28-Diepoxystigmasta-7,92 (11)-diene-3,16,21,24-tetrol

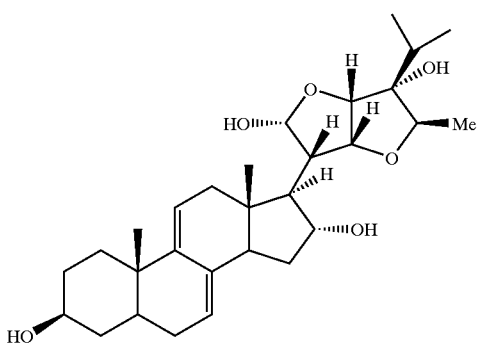

Extraction Procedure

The leaves of the plant *Vernonia amygdalina* were dried and ground to fine particles. The particles (100 g) were soaked in water; ethanol (1l, 1:1 v/v) for 1 hour, after which time the mixture was transferred to a Soxhlet extractor. The resulting mixture was filtered through a Whatman No 1 filter paper and concentrated in vacuo to provide the crude extract (2.3 g). The crude extract (2.3 g) was then purified and fractionated by chromatography furnishing the aforementioned compounds. The compounds were identified by their molecular weight and melting point.

Determination of Biological Effects

The initial extract was orally administered to 26 patients all of whom had been previously diagnosed as suffering from hyperglycemia. A group of 5 control subjects were used who maintained diet discipline throughout the trial. The initial extract was dosed to the patient 3 times daily in 100 mg aliquots for 6 months.

The blood glucose levels of all 31 subjects were closely monitored.

The 26 patients receiving the initial extract no longer required to maintain diet discipline after the first month and examination showed remission of the disease after 3 months.

15 patients continued to receive medication for the remaining 3 months of the trial.

All volunteers now appear to have recovered from the disease and have returned to their normal life prior to the diagnosis of the disease.

What is claimed is:

1. A method for the treatment of hyperglycemia in mammals comprising administering to said mammals a therapeutic amount of a compound, having the formula

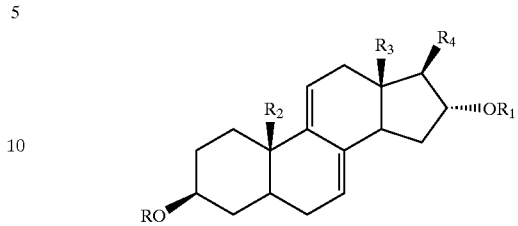

or a pharmaceutically acceptable metal salt thereof, wherein:

R is H or 3-o-β-D-Gluco-pyranoside;
R1 is H, alkyl ($C_1$–$C_4$) or —$OCOCH_3$;
R2 is H or alkyl ($C_1$–$C_4$);
R3 is H or alkyl ($C_1$–$C_4$); and
R4 is Substituent I, Substituent II, Substituent III, Substituent IV or Substituent V, and wherein substituents I, II, III, IV and V are:

Substituent I

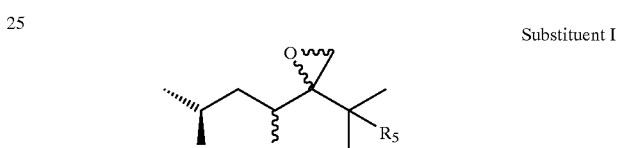

Where $R_5$ = OH or alkyl ($C_1$–$C_4$)

Substituent II

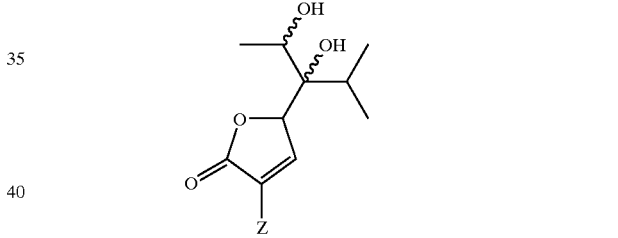

Substituent III

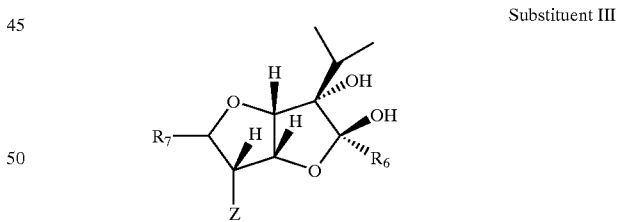

Where $R_6$ is H, OH, or Me
$R_7$ is H, OH or (O═)

Substituent IV

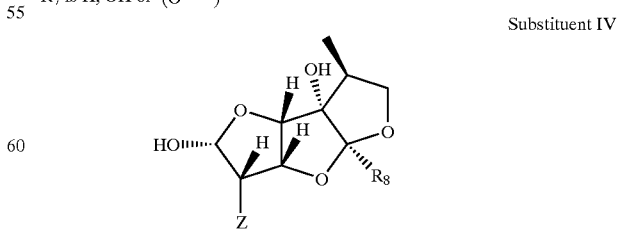

Where $R_8$ is H or alkyl ($C_1$–$C_4$)

Substituent V

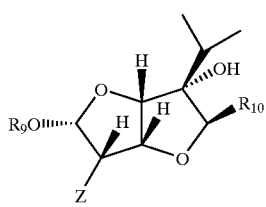

Where R₉ is H, Et, Me and R₁₀ is H, Et, and Me.

2. A method for the treatment of hyperglycemia in mammals as in claim 1, wherein R=H, $R_1$=H, $R_2$=Me, $R_3$=Me and $R_4$=substituent III, in which $R_7$=OH and $R_6$=Me as illustrated below:

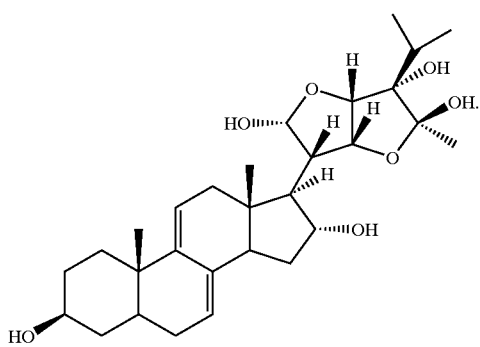

3. A method for the treatment of hyperglycemia in mammals as in claim 1, wherein R=H, $R_1$=H, $R_2$=Me, $R_3$=Me, and $R_4$=substituent I, in which $R_5$=OH as illustrated below:

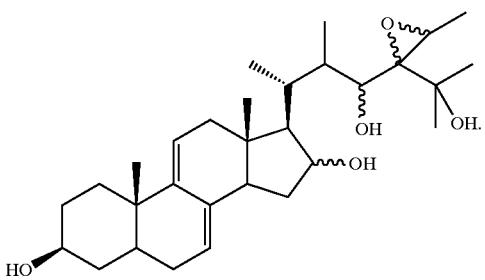

4. A method for the treatment of hyperglycemia in mammals as in claim 1, wherein R=H, $R_1$=H, $R_2$=Me, $R_3$=Me and $R_4$=substituent IV in which $R_8$=Me as illustrated below:

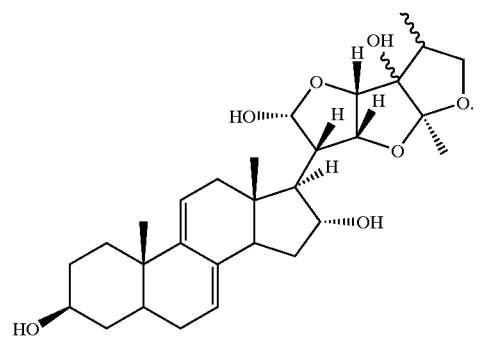

5. A method for the treatment of hyperglycemia in mammals as in claim 1, wherein R=H, $R_1$=H, $R_2$=Me, $R_3$=Me and $R_4$=substituent II as illustrated below:

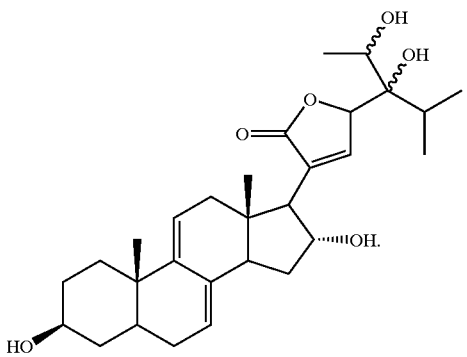

6. A method for the treatment of hyperglycemia in mammals as in claim 1, wherein R=H, $R_1$=H, $R_2$=Me, $R_3$=Me and $R_4$=substituent V in which $R_9$=H and $R_{10}$=Me as illustrated below:

7. A method for the treatment of hyperglycemia in mammals as in claim 1, wherein said compound is in the form of pharmaceutically acceptable cationic salt.

8. A method for the treatment of hyperglycemia in mammals as in claim 1, wherein said compound is in the form of a hydrate.

9. A method for the treatment of hyperglycemia in mammals as in claim 1, wherein said compound is in the form of a solvate.

10. A method for the treatment of hyperglycemia in mammals as in claim 1, further comprising:

a pharmaceutically acceptable carrier, excipient or diluent.

* * * * *